(12) United States Patent
Tsai

(10) Patent No.: US 8,414,659 B2
(45) Date of Patent: Apr. 9, 2013

(54) ANTIBACTERIAL COMPOSITION AND METHODS OF FABRICATING ANTIBACTERIAL TEXTILE

(75) Inventor: Jung-Yu Tsai, Taoyuan County (TW)

(73) Assignee: Taiwan Textile Research Institute, New Taipei (TW)

(*) Notice: Subject to any disclaimer, the term of this patent is extended or adjusted under 35 U.S.C. 154(b) by 85 days.

(21) Appl. No.: 12/330,847

(22) Filed: Dec. 9, 2008

(65) Prior Publication Data
US 2010/0112884 A1    May 6, 2010

(30) Foreign Application Priority Data

Nov. 5, 2008 (TW) .............................. 97142746 A

(51) Int. Cl.
*D06M 11/83* (2006.01)

(52) U.S. Cl.
USPC ........ 8/115.6; 106/1.14; 106/15.05; 106/640; 252/8.61

(58) Field of Classification Search ............ 8/115.6; 252/8.61; 106/1.14, 15.05, 640
See application file for complete search history.

(56) References Cited

U.S. PATENT DOCUMENTS

| | | | | |
|---|---|---|---|---|
| 5,985,308 A | * | 11/1999 | Burrell et al. | 424/426 |
| 7,531,471 B2 | * | 5/2009 | Quincy, III | 442/375 |
| 2004/0106340 A1 | * | 6/2004 | Kreider et al. | 442/117 |
| 2005/0147657 A1 | * | 7/2005 | Canada et al. | 424/445 |

FOREIGN PATENT DOCUMENTS

| | | |
|---|---|---|
| CN | 1730807 | 2/2006 |
| JP | H04-228609 | 8/1992 |
| JP | H05-043414 | 2/1993 |
| JP | H09-228241 | 9/1997 |
| JP | H11-189509 | 7/1999 |
| JP | H11-302119 | 11/1999 |
| JP | 2001-192307 | 7/2001 |
| JP | 2004-161632 | 6/2004 |
| JP | 2005-047884 | 2/2005 |
| JP | 2006-104272 | 4/2006 |
| JP | 2006-282629 | 10/2006 |
| JP | 2007-046184 | 2/2007 |
| JP | 2008-508321 | 3/2008 |
| TW | 200532069 | 10/2005 |

OTHER PUBLICATIONS

"Office Action of Taiwan Counterpart Application", issued on May 24, 2012, p1-p9.
"Office Action of Japan Counterpart Application", issued on Oct. 2, 2012, p1-p3.

* cited by examiner

*Primary Examiner* — Lorna M Douyon
*Assistant Examiner* — Amina Khan
(74) *Attorney, Agent, or Firm* — J.C. Patents

(57) ABSTRACT

An antibacterial composition including silver nano particles, a protective agent and water is provided. The molar ratio of the silver nano particles to the protective agent is 1:0.995-1 and the protective agent is selected from a group consisting of MCl, MBr, MI, $MS_2O_3$ and $NH_4OH$, in which M represents an element of group IA or IIA. Furthermore, two methods of fabricating an antibacterial textile are also provided.

10 Claims, 2 Drawing Sheets

ANTIBACTERIAL COMPOSITION AND METHODS OF FABRICATING ANTIBACTERIAL TEXTILE

CROSS-REFERENCE TO RELATED APPLICATION

This application claims the priority benefit of Taiwan application serial no. 97142746, filed Nov. 5, 2008. The entirety of the above-mentioned patent application is hereby incorporated by reference herein and made a part of this specification.

BACKGROUND OF THE INVENTION

1. Field of the Invention

The present invention generally relates to a composition and methods of fabricating a textile, and in particular, to a composition having antibacterial function and methods of fabricating a low-color distortion antibacterial textile.

2. Description of Related Art

With the improvement of the standard of living, the requirements of a human being on the home environment and personal hygiene conditions have been increased gradually. Numerous products having antibacterial function have got available in daily life. The antibacterial function of various types of products is mostly concerned, and is continuously developed and innovated by the manufactures in various industries.

Silver can damage the cell membrane of bacterium and lead to the necrosis of cells of bacterium, so it has the function of inhibiting bacteria propagation and killing bacteria. Moreover, compared with organic bacteria inhibitors, silver bacteria inhibitors have advantages of low toxicity and long bacteria inhibiting effect. Therefore, the antibacterial and bactericidal effects of numerous daily necessities, such as masks, gauzes, pigments, and plastics are achieved by adding a small amount of silver. Furthermore, nano silver has more active biochemical activity and stronger bactericidal capability, compared with common silver ions or particles. A material, such as plastic, fiber and pigment, can obtain good antibacterial and bactericidal properties by adding a very small amount of nano silver.

However, although nano silver has a good antibacterial efficacy, a quite troublesome problem, i.e. yellowing, occurs when being used in a textile. A textile desired to have antibacterial effect can get antibacterial effect by being immersed in a solution containing silver ions. However, accompanying yellow spots are generated on the textile, which is aesthetically unpleasant in appearance. Furthermore, the generation of yellowing is quite fast, and almost occurs within 12 hours. Nano silver has quite excellent antibacterial efficacy when being applied in textile, but the antibacterial function of nano silver can be applied in textile only on condition that the problem of yellowing is overcame.

SUMMARY OF THE INVENTION

Accordingly, the present invention is directed to an antibacterial composition, which can reduce the opportunity of yellowing.

The present invention is directed to methods of fabricating a low-color distortion antibacterial textile having antibacterial efficacy and being not likely to have yellowing occur.

The present invention provides an antibacterial composition, including silver nano particles, a protective agent, and water. The molar ratio of the silver nano particles to the protective agent is 1:0.995-1, and the protective agent is selected from a group consisting of MCl, MBr, MI, $MS_2O_3$ and $NH_4OH$, in which M represents an element of group IA or IIA.

In an embodiment of the present invention, the protective agent has at least two or more components selected from MCl, MBr, MI, $MS_2O_3$, and $NH_4OH$.

In an embodiment of the present invention, the concentration of free active silver ions released by the silver nano particles in the antibacterial composition is 0-2 ppm.

In an embodiment of the present invention, the concentration of the silver nano particles in the antibacterial composition is 30-100 ppm.

The present invention provides a method of fabricating a low-color distortion antibacterial textile. First, a textile substrate is provided. Next, an antibacterial composition including silver nano particles, a protective agent, and water is prepared. Specifically, the molar ratio of the silver nano particles to the protective agent is 1:0.995-1, and the protective agent is selected from a group consisting of MCl, MBr, MI, $MS_2O_3$ and $NH_4OH$, in which M represents an element of group IA or IIA. Then, the antibacterial composition is applied onto the surface of the textile substrate.

In an embodiment of the present invention, the protective agent has at least two or more components selected from MCl, MBr, MI, $MS_2O_3$, and $NH_4OH$.

In an embodiment of the present invention, the concentration of free active silver ions released by the silver nano particles in the antibacterial composition is 0-2 ppm.

In an embodiment of the present invention, the concentration of the silver nano particles in the antibacterial composition is 30-100 ppm.

In an embodiment of the present invention, the antibacterial composition further includes an adhesive resin at a concentration of 2-5%.

In an embodiment of the present invention, the method of applying the antibacterial composition onto the surface of the textile substrate includes dip dyeing, coating, padding, or printing.

In an embodiment of the present invention, the fabrication method further includes performing a washing procedure and performing an antibacterial function test procedure.

The present invention further provides another method of fabricating a low-color distortion antibacterial textile. First, an antibacterial composition is prepared. The antibacterial composition includes silver nano particles, a protective agent, and water. The molar ratio of the silver nano particles to the protective agent is 1:0.995-1, and the protective agent is selected from a group consisting of MCl, MBr, MI, $MS_2O_3$ and $NH_4OH$, in which M represents an element of group IA or IIA. Next, a textile fiber is provided. Then, the antibacterial composition is applied onto the surface of the textile fiber.

In an embodiment of the present invention, the protective agent has at least two or more components selected from MCl, MBr, MI, $MS_2O_3$, and $NH_4OH$.

In an embodiment of the present invention, the concentration of free active silver ions released by the silver nano particles in the antibacterial composition is 0-2 ppm.

In an embodiment of the present invention, the concentration of the silver nano particles in the antibacterial composition is 30-100 ppm.

In an embodiment of the present invention, the antibacterial composition further includes an adhesive resin at a concentration of 2-5%.

In an embodiment of the present invention, the method of applying the antibacterial composition onto the surface of the textile fiber includes dip dyeing, coating, padding, or printing.

In an embodiment of the present invention, the method of fabricating the low-color distortion antibacterial textile further includes performing a washing procedure and performing an antibacterial function test procedure.

In an embodiment of the present invention, the method of fabricating the low-color distortion antibacterial textile further includes performing a textile chromaticity test procedure.

Based on above, the antibacterial composition of the present invention includes a protective agent and silver nano particles, in which the protective agent can reduce the opportunity of yellowing. The textile fabricated by the methods of fabricating a low-color distortion antibacterial textile of the present invention has antibacterial function and reduced opportunity of yellowing.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
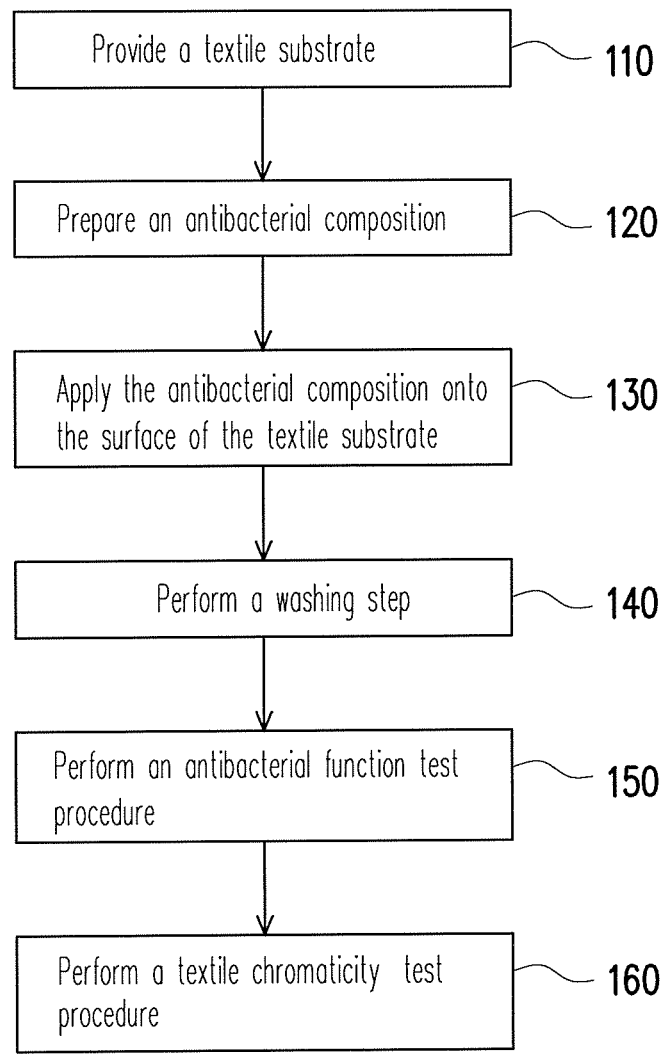
FIG. 1 is a flow chart of a method of fabricating a low-color distortion antibacterial textile according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

The antibacterial composition according to an embodiment of the present invention includes silver nano particles, a protective agent, and water. It should be noted that, the molar ratio of the silver nano particles to the protective agent is 1:0.995-1. The protective agent is selected from a group consisting of MCl, MBr, MI, $MS_2O_3$, and $NH_4OH$, in which M represents an element of group IA (e.g. lithium, sodium, and potassium) or group IIA (e.g. beryllium, magnesium, and calcium).

Table 1 shows the experiment result of an antibacterial effect test of the protective agent and the antibacterial composition of this embodiment. The specific experimental scheme is as follows. The substrates to be processed are processed with the protective agent (KI) and the antibacterial composition of the present invention, and the useful substrates to be processed are cotton. The processing conditions include: padding first, and then drying at a temperature of 160° C. for 3 min. After the processing, the degree of yellowing is observed. Afterwards, the degree of yellowing degree is further observed after irradiation with sunlight. Furthermore, the AATCC100 *Staphyloccocus aureus* sterilization rate experiment is performed to detect antibacterial level. The protective agent ingredient used in the experiment is potassium iodide (KI). Generally, iodide ions ($I^-$) released when dissolving potassium iodide into a solvent to form a solution have bactericidal effect. The experiment above is performed in order to find out whether the antibacterial effect of the antibacterial composition of this embodiment is resulted from the iodide ions in the protective agent or not. However, it can be known clearly from the result in Table 1 that, the antibacterial effect of the antibacterial composition of this embodiment is obviously better than that of the protective agent alone. Therefore, it is proved that, the antibacterial effect of the antibacterial protective agent in the embodiment is not resulted from the protective agent, and the antibacterial composition of the antibacterial composition of the present invention substantially has antibacterial efficacy.

TABLE 1

| Solution Composition | Nano Silver 45 ppm and Protective Agent (KI) 71.4 ppm | Protective Agent (KI) 71.4 ppm |
|---|---|---|
| Substrate to be Processed | Cotton | Cotton |
| Processing Manner | Padding, drying at 160° C., 3 min | Padding, drying at 160° C., 3 min |
| Post-processing Appearance Observation | No obvious yellowing | Serious yellowing |
| Post-sunlight Irradiation Appearance Observation | No obvious yellowing | Serious yellowing |
| AATCC100 *Staphyloccocus aureus* Sterilization Rate | 99.4% | <0 |

In this embodiment, the concentration of the free active silver ions released by the silver nano particles in the antibacterial composition is 0-2 ppm. In particular, in this embodiment, the concentration of the silver nano particles in the antibacterial composition is between 30 ppm and 100 ppm. In this embodiment, the protective agent preferably has at least two or more components selected from MCl, MBr, MI, $MS_2O_3$, and $NH_4OH$. As described above, M represents an element of group IA or IIA. Because the components in the protective agent mentioned above has different binding rate and disassociation rate to the silver nano particles in the protective agent, the more the component types used in the protective agent is, the better the yellowing resistant effect of the antibacterial composition is.

Table 2 shows the experiment result of an antibacterial effect test and the concentration of silver ions on the substrates. One substrate is processed with the antibacterial composition having the protective agent therein, the other substrate is processed with only silver nano particles, and the useful substrates to be processed are cotton. The processing conditions include: padding first, and then drying at a temperature of 160° C. for 3 min. After the processing, the degree of yellowing is observed. In addition, the concentration of silver ions on the substrate processed after 1 day is detected with dipping the substrate in water (1 g/100 ml) for 18-24 hours, and then detecting the concentration of silver ions with an instrument (DR4000U spectrophotometer 3400 silver program, manufactured by HACH company). Furthermore, the AATCC100 *Staphyloccocus aureus* sterilization rate experiment is performed to detect antibacterial level. It can be known clearly from the result in Table 2 that, the degree of yellowing of the antibacterial composition having the protective agent therein is obviously better than that of nano silver particles alone. In particular, the silver ions released from the antibacterial composition having the protective agent therein is slower than that released from nano silver particles alone, and therefore the antibacterial composition having the protective agent therein may provide a longer period of time of protecting. Furthermore, in the embodiment, the concentration of released silver ions of the antibacterial composition is much lower than 50 ng/kg, and thus it meets the environmental protection requirements in America and Europe.

TABLE 2

| Solution Composition | Nano Silver 30 ppm and Protective Agent (KI) 0.01% | Nano Silver 30 ppm |
|---|---|---|
| Substrate to be Processed | Cotton | Cotton |
| Processing Manner | Padding, drying at 160° C., 3 min | Padding, drying at 160° C., 3 min |
| Post-processing Appearance Observation | No obvious yellowing | Serious yellowing |
| Concentration of Silver Ions on the Substrate Processed after 1 day | 0.006 ppm/g (0.6 ng/kg) | 0.27 ppm/g (27 ng/kg) |
| AATCC100 *Staphyloccocus aureus* Sterilization Rate | >99.9% | >99.9% |

Table 3 shows the experiment result of yellowing resistant effect of the antibacterial composition at different concentrations of the protective agent. The textile substrate used in the experiment is cotton. The components of the protective agent are sodium chloride (NaCl), sodium thiosulfate ($Na_2S_2O_3$) and potassium iodide (KI), and the content of the nano silver in the antibacterial composition is 30 ppm. The yellowing degree is determined with CIE whiteness value. In the embodiment, the CIE whiteness value is measured with an instrument (SF600 PLUS spectraflash, manufactured by datacolor company). The higher the whiteness value is, the whiter the object is, and the smaller the difference between two whiteness values is, the lower the color distortion degree is. It can be clearly seen from the experimental data in Table 3 that the concentration of the protective agent in the antibacterial composition is positive correlated with the yellowing resistant effect. That is to say, the antibacterial composition has good yellowing resistant effect, when the concentration of the protective agent is high.

TABLE 3

| Percentage of Protective Agent in Antibacterial Composition (%) | 2.1 | 1.6 | 1.1 | 0.6 | 0.1 |
|---|---|---|---|---|---|
| CIE Whiteness Value (prior sunlight irradiation) | 82.0 | 78.3 | 74.9 | 70.8 | 68.7 |
| CIE Whiteness Value (post sunlight irradiation) | 80.6 | 76.1 | 67.9 | 63.4 | 48.3 |
| Whiteness Value Difference | -1.4 | -2.2 | -7 | -7.4 | -20.4 |

In the embodiment above, the protective agent in the antibacterial composition has chelating effect on the silver nano particles, or the free active silver ions released by the silver nano particles, such that the antibacterial composition has yellowing resistant property. The antibacterial composition is applicable in the textile due to the advantage of yellowing resistance, such that the textile has antibacterial effect and is not likely to have yellowing occur. Hereinafter, several implementations of the methods of fabricating a low-color distortion antibacterial textile will be illustrated in detail in the following embodiments.

FIG. 1 is a flow chart of a method of fabricating a low-color distortion antibacterial textile according to an embodiment of the present invention. Referring to FIG. 1, the method of fabricating a low-color distortion antibacterial textile includes the following steps. First, Step 110 of providing a textile substrate is performed. The textile substrate is, for example, cotton, nylon, or other suitable textile materials.

Next, Step 120 of preparing an antibacterial composition, for example, one described in the previous embodiment, is performed. Preferably, the protective agent in the antibacterial composition has at least two or more components selected from MCl, MBr, MI, $MS_2O_3$, and $NH_4OH$, in which M represents an element of group IA or IIA. In this embodiment, the concentration of the free active silver ions released by the silver nano particles in the antibacterial composition is 0-2ppm. In particular, in this embodiment, the concentration of the silver nano particles in the antibacterial composition is between 30 ppm and 100 ppm.

Afterwards, Step 130 of applying the antibacterial composition onto the surface of the textile substrate is performed. The antibacterial composition of this embodiment further includes an adhesive resin, such that the antibacterial composition has a preferred adhesion capability on the textile substrate. Preferably, the concentration of the adhesive resin is 2-5%. In this embodiment, the method of applying the antibacterial composition onto the surface of the textile substrate is, for example dip dyeing, coating, padding, or printing.

The method of fabricating a low-color distortion antibacterial textile of this embodiment further includes performing a washing procedure and an antibacterial function test procedure. As shown in Step 140, the washing step removes the remaining antibacterial composition after applying the antibacterial composition onto the textile substrate. Furthermore, as shown in Step 150, the antibacterial function test is to make certain whether the antibacterial textile still has antibacterial efficacy after the previous implementation steps. Table 4 shows the experiment result of the AATCC100 *Staphyloccocus aureus* sterilization rate test of the antibacterial textile of this embodiment after 30-time AATCC135 washing. It can be known from the experiment result of Table 4 that, the antibacterial textile of this embodiment still has considerably obvious antibacterial effect after washing.

TABLE 4

| Textile Substrate | Cotton |
|---|---|
| Processing Manner | Padding, drying at 160° C., 3 min |
| AATCC100 *Staphyloccocus aureus* Sterilization Rate after 30-time AATCC135 Washing | 96.8% |

The method of fabricating a low-color distortion antibacterial textile of this embodiment can further include a textile chromaticity test procedure, as shown in Step 160. Table 5 shows the experiment result of the chromaticity test of the antibacterial textile of this embodiment and a control group. The textile substrate used in the experiment is cotton, and the experimental condition is irradiation with sunlight for 8 days. CIE whiteness values are determined before irradiation with sunlight and then again after 8 days irradiation with sunlight. The higher the whiteness value is, the whiter the object is, and the smaller the difference of the whiteness values is, the lower the color distortion degree is. It can be clearly known from the experiment result in Table 5 that, the antibacterial textile fabricated by the method of fabricating a antibacterial textile of this embodiment has a whiteness value of 82.7 after 8-day irradiation with sunlight, which is higher than 75, and the difference of the irradiation whiteness values prior and post sunlight irradiation is 3.5 and in the range of ±5. This indicates that the antibacterial textile fabricated in this embodiment has quite excellent yellowing resistant effect almost having no color distortion occur.

TABLE 5

|  | Control Group | Antibacterial Textile of this Embodiment |
|---|---|---|
| Textile Substrate | Cotton | Cotton |
| Processing Manner | Drying at 160° C., 3 min | Padding, drying at 160° C., 3 min |
| CIE Whiteness Value (prior sunlight irradiation) | N/A | 79.2 |
| CIE Whiteness Value (post sunlight irradiation) | 79.1 | 82.7 |
| CIE Whiteness Value Difference | N/A | 3.5 |

In this embodiment, the detailed implementation of the application of the antibacterial composition in fabrication of textile is provided. Moreover, it is proved by the experiment data that antibacterial textile of this embodiment substantially has antibacterial efficacy. Most importantly, in addition to the antibacterial function, the antibacterial textile of this embodiment has low occurrence opportunity of yellowing. In the following embodiment, another method of fabricating a low-color distortion antibacterial textile will be further illustrated. It should be noted and emphasized that, the antibacterial processing is performed at the initial stage of the fabrication of the textile, namely, at the step of providing a textile fiber.

Figure 2:
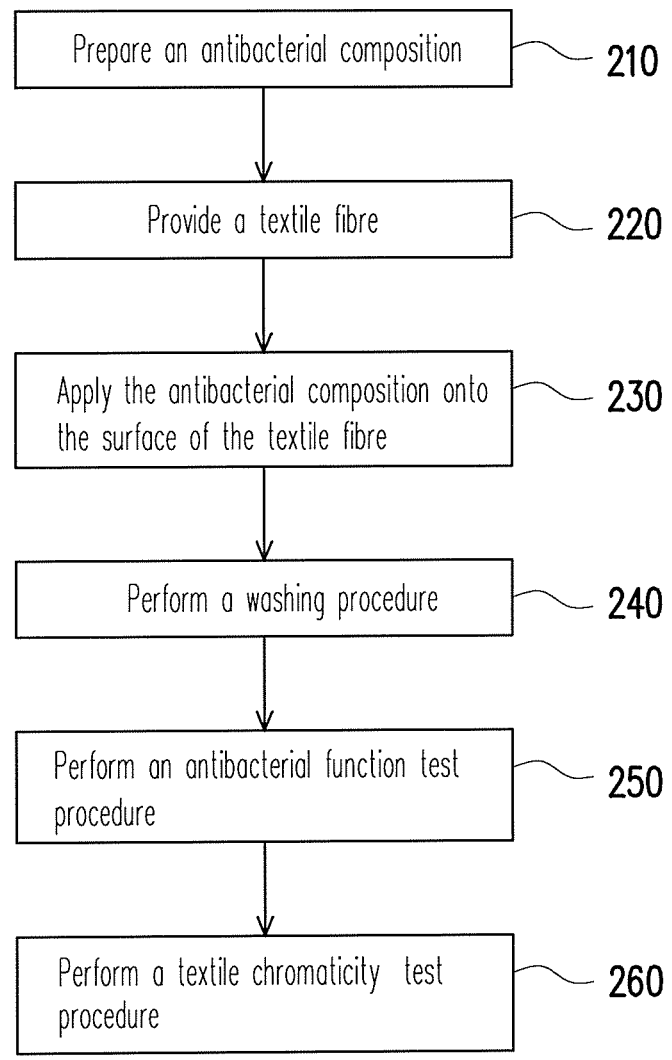
FIG. 2 is a flow chart of another method of fabricating a low-color distortion antibacterial textile according to an embodiment of the present invention.

FIG. 2 is a flow chart of another method of fabricating a low-color distortion antibacterial textile according to an embodiment of the present invention. Referring to FIG. 2, the method of fabricating a low-color distortion antibacterial textile of this embodiment includes the following steps. First, Step 210 of preparing an antibacterial composition is performed. In this embodiment, the specific components of the antibacterial composition can be known with reference to the antibacterial composition mentioned in the previous embodiment and will not be repeated herein. Preferably, the protective agent in the antibacterial composition has at least two or more compounds selected from MCl, MBr, MI, $MS_2O_3$, and $NH_4OH$, in which M represents an element of group IA or IIA.

Next, Step 220 of providing a textile fiber is performed. The textile fiber of this embodiment is, for example, polyester, cotton yarn, or other suitable textile fibers.

Then, Step 230 of applying the antibacterial composition onto the surface of the textile fiber is performed. The antibacterial composition of this embodiment further includes an adhesive resin at a suitable concentration of 2-5%, in order to improve the adhesion capability of the antibacterial composition on the textile fiber. In this embodiment, the method of applying the antibacterial composition onto the surface of the textile fiber is, for example, dip dyeing, coating, padding, or printing.

Similar to the method of fabricating an antibacterial textile mentioned above, the method of fabricating a low-color distortion antibacterial textile of this embodiment further includes Step 240 of performing a washing procedure. The fabrication method of this embodiment also includes Step 250 of performing an antibacterial function test procedure. Moreover, Step 260 of performing a textile chromaticity test procedure is further included. The purpose and detailed operation of performing the steps can be known with reference to the previous embodiment, and will not be repeated herein.

In view of the above, the antibacterial composition of the present invention has a protective agent selected from a group consisting of MCl, MBr, MI, $MS_2O_3$ and $NH_4OH$, in which M represents an element of group IA or IIA. The protective agent functions to reduce the opportunity of yellowing. The methods of fabricating a low-color distortion antibacterial textile of the present invention use the antibacterial composition, thus the fabricated textile has antibacterial efficacy and low opportunity of yellowing.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of fabricating a low-color distortion antibacterial textile, comprising:
   providing a textile substrate;
   preparing an antibacterial composition, comprising:
      silver nano particles;
      a protective agent, wherein a molar ratio of the silver nano particles to the protective agent is 1:0.995-1, the protective agent comprises at least two or more components selected from a group consisting of MCl, MBr, MI, $MS_2O_3$, and $NH_4OH$, and M represents an element of group IA or IIA, wherein the at least two or more components in the protective agent have different binding rate and disassociation rate to the silver nano particles, such that a concentration of free active silver ions released by the silver nano particles in the antibacterial composition is 0.27~2 ppm, wherein a concentration of the silver nano particles in the antibacterial composition is 30 ppm; and
      water; and
   applying the antibacterial composition onto a surface of the textile substrate.

2. The method of fabricating a low-color distortion antibacterial textile according to claim 1, wherein the antibacterial composition further comprises an adhesive resin with a concentration of 25%.

3. The method of fabricating a low-color distortion antibacterial textile according to claim 1, wherein a method of applying the antibacterial composition onto the surface of the textile substrate comprises dip dyeing, coating, padding, or printing.

4. The method of fabricating a low-color distortion antibacterial textile according to claim 1, further comprising:
   performing a washing procedure; and
   performing an antibacterial function test procedure.

5. The method of fabricating a low-color distortion antibacterial textile according to claim 1, further comprising performing a textile chromaticity test procedure.

6. A method of fabricating a low-color distortion antibacterial textile, comprising:
   preparing an antibacterial composition, comprising:
      silver nano particles;
      a protective agent, wherein a molar ratio of the silver nano particles to the protective agent is 1:0.9951 and the protective agent comprises at least two or more components selected from a group consisting of MCl, MBr, MI, $MS_2O_3$ and $NH_4OH$, and M represents an element of group IA or IIA, wherein the at least two or more components in the protective agent have different binding rate and disassociation rate to the silver nano particles, such that a concentration of free active silver ions released by the silver nano particles in the antibacterial composition is 0.27~2 ppm, wherein a concentration of the silver nano particles in the antibacterial composition is 30 ppm; and water;
providing a textile fiber; and
applying the antibacterial composition onto a surface of the textile fiber.

7. The method of fabricating a low-color distortion antibacterial textile according to claim 6, wherein the antibacterial composition further comprises an adhesive with a concentration of 25%.

8. The method of fabricating a low-color distortion antibacterial textile according to claim 6, wherein a method for applying the antibacterial composition onto the surface of the textile fiber comprises dip dyeing, coating, padding, or printing.

9. The method of fabricating a low-color distortion antibacterial textile according to claim 6, further comprising:
performing a washing procedure; and
performing an antibacterial function test procedure.

10. The method of fabricating a low-color distortion antibacterial textile according to claim 6, further comprising performing a textile chromaticity test procedure.

* * * * *